United States Patent [19]
Didier et al.

[11] Patent Number: 5,962,705
[45] Date of Patent: Oct. 5, 1999

[54] PROCESS FOR PREPARING DERIVATIVES OF THE TAXOID FAMILY

[75] Inventors: Eric Didier, Paris; Gilles Oddon, Lyon; Denis Pauze, Solaize; Patrick Leon, Tassin La Demi Lune; Didier Riguet, Serezin Du Rhone, all of France

[73] Assignee: Rhone-Poulenc Rorer S.A., Antony Cedex, France

[21] Appl. No.: 09/192,502

[22] Filed: Nov. 17, 1998

[30] Foreign Application Priority Data

Nov. 18, 1997 [FR] France .................. 97 14442

[51] Int. Cl.$^6$ ............... C07D 305/14; C07D 263/06
[52] U.S. Cl. .............. 549/510; 549/511; 548/215
[58] Field of Search ................... 549/510, 511

[56] References Cited

U.S. PATENT DOCUMENTS

| | | | |
|---|---|---|---|
| 3,927,118 | 12/1975 | Ozretich | 260/613 D |
| 5,008,454 | 4/1991 | Inoue et al. | 564/294 |

FOREIGN PATENT DOCUMENTS

| | | |
|---|---|---|
| 0400971B1 | 12/1990 | European Pat. Off. . |
| 0617018A1 | 9/1994 | European Pat. Off. . |
| 0728724A1 | 8/1996 | European Pat. Off. . |
| WO 94/07878 | 4/1994 | WIPO . |
| WO 95/25728 | 9/1995 | WIPO . |
| WO 95/29926 | 11/1995 | WIPO . |
| WO 96/30355 | 10/1996 | WIPO . |

*Primary Examiner*—Ba K. Trinh
*Attorney, Agent, or Firm*—Finnegan, Henderson, Farabow, Garrett & Dunner, L.L.P.

[57] ABSTRACT

The present invention relates to a novel process for preparing dialkoxy derivatives of the taxoid family by direct alkylation of the two positions 7 and 10 of deacetylbaccatin or derivatives thereof which are esterified in position 13.

24 Claims, No Drawings

PROCESS FOR PREPARING DERIVATIVES OF THE TAXOID FAMILY

The present invention relates to a novel process for preparing dialkoxy derivatives of the taxoid family. The expression dialkoxy derivatives of the taxoid family is understood to refer to derivatives bearing an alkoxy unit in positions 7 and 10 of the baccatin ring-system and optionally bearing a β-phenylisoserine chain in position 13.

More specifically, the expression dialkoxy derivatives of the taxoid family is understood to refer to the derivatives corresponding to the following general formula:

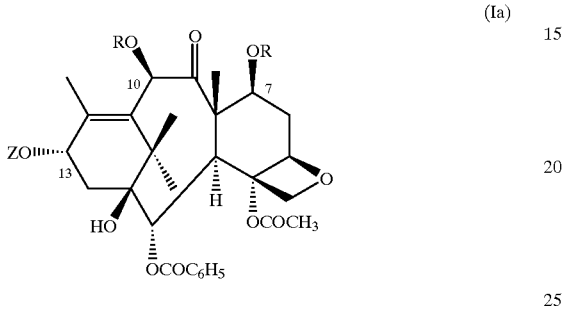

(Ia)

in which:
the groups R represent the same straight or branched alkyl group containing 1 to 6 carbon atoms
Z represents hydrogen or a unit of formula

(Ib)

in which $R_1$ represents
1) a straight or branched alkyl radical containing 1 to 8 carbon atoms, a straight or branched alkenyl radical containing 2 to 8 carbon atoms, a straight or branched alkynyl radical containing 2 to 8 carbon atoms, a cycloalkyl radical containing 3 to 6 carbon atoms, a phenyl or α- or β-naphthyl radical optionally substituted with one or more atoms or radicals chosen from halogen atoms and alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro and trifluoromethyl radicals, or
2) a 5-membered aromatic heterocycle containing one or more hetero atoms, which may be identical or different, chosen from nitrogen, oxygen and sulphur atoms, and optionally substituted with one or more substituents, which may be identical or different, chosen from halogen atoms and alkyl, aryl, amino, alkylamino, dialkylamino, alkoxycarbonylamino, acyl, arylcarbonyl, cyano, carboxyl, carbamoyl, alkylcarbamoyl, dialkylcarbamoyl, and alkoxycarbonyl radicals,
3) it being understood that, in the substituents on the phenyl, α- or β-naphthyl radicals and the aromatic heterocycles, the alkyl radicals and the alkyl portions of the other radicals contain 1 to 4 carbon atoms and that the alkenyl and alkynyl radicals contain 2 to 8 carbon atoms and that the aryl radicals are phenyl or α- or β-naphthyl radicals, $R_2$ represents
1) a benzoyl radical optionally substituted with one or more atoms or radicals, which may be identical or different, chosen from halogen atoms and alkyl radicals containing 1 to 4 carbon atoms, alkoxy radicals containing 1 to 4 carbon atoms or trifluoromethyl, thenoyl or furoyl radicals, or
2) a radical $R'_2$-O-CO- in which $R'_2$ represents: an alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, these radicals optionally being substituted with one or more substituents chosen from halogen atoms and hydroxyl radicals, alkoxy radicals containing 1 to 4 carbon atoms, dialkylamino radicals in which each alkyl part contains 1 to 4 carbon atoms, piperidino or morpholino radicals, 1-piperazinyl radicals (optionally substituted in position 4 with an alkyl radical containing 1 to 4 carbon atoms or with a phenyl alkyl radical in which the alkyl part contains 1 to 4 carbon atoms), cycloalkyl radicals containing 3 to 6 carbon atoms, cycloalkenyl radicals containing 4 to 6 carbon atoms, phenyl radicals (optionally substituted with one or more atoms or radicals chosen from halogen atoms and alkyl radicals containing 1 to 4 carbon atoms or alkoxy radicals containing 1 to 4 carbon atoms), cyano or carboxyl radicals or alkoxycarbonyl radicals in which the alkyl part contains 1 to 4 carbon atoms, a phenyl or α- or β-naphthyl radical optionally substituted with one or more atoms or radicals chosen from halogen atoms and alkyl radicals containing 1 to 4 carbon atoms or alkoxy radicals containing 1 to 4 carbon atoms or a 5-membered aromatic heterocyclic radical preferably chosen from furyl and thienyl radicals, or a saturated heterocyclic radical containing 4 to 6 carbon atoms, optionally substituted with one or more alkyl radicals containing 1 to 4 carbon atoms.

Among the products of formula (Ia) which are the subject of the process of the present invention, the preferred ones are those for which:
Z represents hydrogen or a radical of formula (Ib) in which
$R_1$ represents a phenyl radical
$R_2$ represents a tert-butoxycarbonyl radical or a benzoyl radical.

The products most particularly preferred are those for which:
$R_1$ represents a phenyl radical
$R_2$ represents a tert-butoxycarbonyl radical
R represents a methyl radical.

It is known practice, according to patent WO 96/30355, to prepare a derivative according to the present invention by two processes. According to a first, multi-step process, starting with 10-deacetylbaccatin III of formula:

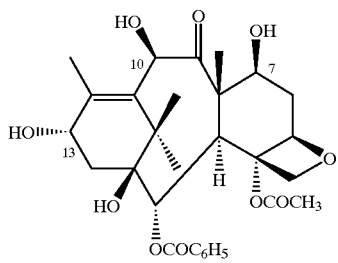

(II)

it is selectively protected in positions 7 and 13, for example in the form of a disilyl ether, followed by the action of a product of general formula:

R—X  (III)

in which R represents a radical as defined above and X represents a reactive ester residue such as a sulphuric or sulphonic ester residue, or a halogen atom, to give a product bearing the unit —OR in position 10 and silyl groups in positions 7 and 13. Next, the silyl protecting groups are replaced with hydrogen atoms to give a compound still bearing the group —OR in position and OH groups in positions 7 and 13. This derivative is selectively etherified in position 7 by reaction with the derivative of formula (III) to give the derivative of formula (I) in which Z is equal to hydrogen.

The final step consists in esterifying in position 13, according to a process which is known per se, the derivatives of formula (Ia), in which Z represents hydrogen, in the presence of a β-lactam, for example according to the process described in patent EP 617,018, or in the presence of an oxazolidine, for example according to the process described in patent Wo 96/30355 mentioned above.

According to a second process described in the same patent WO 96/30355, the products of general formula (Ia) can be obtained according to a 5-step process starting from the product of general formula (II). In a first step, protection of positions 7 and 10 is carried out, followed by esterification at position 13 in the presence of a β-lactam, for example according to the process described in patent EP 617,018, or in the presence of an oxazolidine, for example as described in patent WO 96/30355 mentioned above. After deprotection of the protecting groups in positions 7 and 10, an ester of formula (Ia) is thus obtained in which Z is other than hydrogen and R represents hydrogen. The following step consists in reacting positions 7 and 10 simultaneously by the action of a reagent formed in situ from a sulphoxide of formula (IV) and acetic anhydride (Pummerer-type reaction),

R—SO—R  (IV)

in which R has the same meaning as above, in order to form an alkylthioalkyloxy type intermediate on positions 7 and 10.

The final step which gives the desired compound of formula (Ia) is carried out on the intermediate compound obtained above by the action of activated Raney nickel.

Generally, the action of the reagent formed in situ from the sulphoxide of general formula (IV), preferably dimethyl sulphoxide and acetic anhydride, is carried out in the presence of acetic acid or an acetic acid derivative such as a haloacetic acid, at a temperature of between 0 and 50° C.

Generally, the action of activated Raney nickel in the presence of an aliphatic alcohol or an ether is carried out at a temperature of between −10 and 60° C.

The set of processes described in this prior art has never made it possible to reach directly, in one step, the dialkoxy derivatives in positions 7 and 10 of 10-deacetylbaccatin III.

The present invention makes it possible to achieve this aim. It allows the selective and simultaneous, direct one-step alkylation of the two hydroxyl functions in positions 7 and 10 of 10-deacetylbaccatin or derivatives thereof which are esterified in position 13, of formula (V)

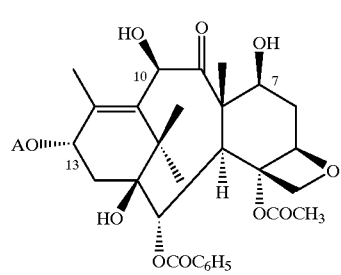

(V)

in which A represents hydrogen or aside chain of formula (Ic) below:

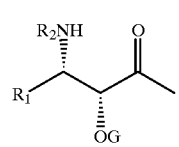

(Ic)

in which G represents a protecting group for the hydroxyl function or an oxazolidine unit of formula (Id):

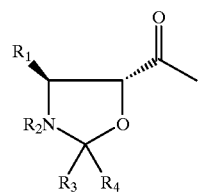

(Id)

in which $R_1$ and $R_2$ have the same meanings as above and $R_3$ and $R_4$ are chosen from hydrogen or from alkyl, aryl, halo, alkoxy, arylalkyl, alkoxyaryl, haloalkyl and haloaryl radicals, it being possible for the substituents optionally to form a 4- to 7-membered ring.

It is preferred to use lo-deacetylbaccatin as starting material, i.e. the product of formula (II), which makes the process considerably cost-effective and moreover avoids the intermediate protection and deprotection steps required in the processes of the prior art.

Among the groups G for protecting the hydroxyl function in formula (Ic), it is generally preferred to select the set of protecting groups described in books such as Greene and Wuts Protective Groups in Organics Synthesis 1991, John Wiley & Sons, and MacOmie, Protective Groups in Organic Chemistry, 1975, Plenum Press, and which are deprotected under conditions which degrade the rest of the molecule little or not at all, such as, for example:

ethers and preferably ethers such as methoxymethyl ether, 1-ethoxyethyl ether, benzloxymethyl ether, p-methoxybenzyloxymethyl ether, benzyl ethers optionally substituted with one or more groups such as methoxy, chloro or nitro, 1-methyl-1-methoxyethyl ether, 2-(trimethylsilyl)ethoxymethyl ether, tetrahydropyranyl ether or silyl ethers such as trialkylsilyl ethers, carbonates such as trichloroethyl carbonates.

More particularly, the radicals $R_3$ and $R_4$ of the general formula (Id) are chosen from those described in patent WO 94/07878, and the derivatives in which $R_3$ is hydrogen and $R_4$ is a p-methoxyphenyl radical are more particularly preferred.

The alkylating agent is chosen from:

alkyl halides and preferably, among those, alkyl iodides (RI)

alkyl sulphates such as methyl-sulphate oxoniums such as boric salts of trialkyloxoniums, in particular trimethyloxonium tetrafluoroborate ($Me_3OBF_4$).

Methyl iodide is preferably used.

The alkylating agent is used in the presence of an anionization agent such as one or more strong bases in anhydrous medium.

Among the bases which can be used in anhydrous medium, mention may be made of:

alkali metal hydrides such as sodium or potassium hydride alkali metal alkoxides such as potassium tert-butoxide silver oxide $Ag_2O$ 1,8-bis(dimethylamino)naphthalene mixtures of mono- or bimetallic base such as those described, for example, in publications such as P. Caubère Chem. Rev. 1993, 93, 2317–2334 or M. Schlosser Mod. Synth. Methods (1992), 6, 227–271; in particular, the alkyllithium/alkali metal t-butoxide or alkali metal amides/alkali metal t-butoxide combinations are preferred. One of the two bases can be generated "in situ".

Among all of the possible combinations of alkylating agent and anionization agent, it is preferred to use methyl iodide in the presence of potassium hydride.

Preferably, the reaction is carried out in an organic medium which is inert under the reaction conditions. Among the solvents, it is preferred to use:

ethers such as tetrahydrofuran or dimethoxyethane when silver oxide is used, it is preferred to use polar aprotic solvents such as dimethylformamide or aromatic solvents such as toluene when 1,8-bis(dimethylamino)naphthalene is used, it is preferred to use esters, for example alkyl esters such as ethyl acetate.

For better implementation of the invention, it is preferred to use a molar ratio between the anionization agent and the substrate of greater than 2 and preferably between 2 and 20.

It is also preferred to use a molar ratio between the alkylating agent and the substrate of greater than 2 and preferably between 2 and 40.

It is preferred to use a reaction temperature of between −30° C. and 80° C.

The reaction time advantageously ranges between a few hours and 48 hours depending on the reagents chosen.

After the alkylation step, when the latter is carried out on 10-deacetylbaccatin, the esterification step is then performed in a known manner, for example according to the processes described in patents EP 617,018 or WO 96/30355 mentioned above.

Thus, according to a first three-step process, 10-deacetylbaccatin is used to begin with, first carrying out the dialkylation using an alkylating agent in the presence of a strong base, and in a second step the 10-deacetylbaccatin dietherified in positions 7 and 10 is coupled in position 13 with a suitably protected β-lactam in the presence of an activating agent chosen from tertiary amines and metallic bases, to form an alkoxide in position 13. The side chain is then deprotected by the action of an inorganic or organic acid.

Thus, according to a second three-step process, 10-deacetylbaccatin is used to begin with, first carrying out the dialkylation using an alkylating agent in the presence of a strong base, and in a second step the 10-deacetylbaccatin dietherified in positions 7 and 10 is coupled in position 13 with an oxazolidine in the presence of a coupling agent such as diimides in the presence of an activating agent such as dialkylaminopyridines. The oxazolidine is opened by the action of an inorganic or organic acid.

According to a third process, the baccatin suitably protected in positions 7 and 10 is first esterified in position 13 with a β-lactam or an oxazolidine in the presence of a coupling agent and/or an activating agent as described in the above two processes. After deprotection in positions 7 and 10, the dietherification in positions 7 and 10 is carried out with an alkylating agent in the presence of a strong base. The side chain is then deprotected by the action of an inorganic or organic acid.

The present invention will be described more fully with the aid of the examples which follow, which should not be considered as limiting the invention.

EXAMPLES

All of these tests are carried out under argon and using anhydrous solvents.

Example 1

Silver oxide/methyl iodide/toluene/10-DAB

Silver oxide (255 mg, 1.1 mmol, 2.2 equiv.) is added to a suspension of 10-deacetylbaccatin III (272 mg, 0.5 mmol) in a toluene/methyl iodide mixture (3/2; 2.5 ml) at 0° C. The mixture is allowed to return gradually to room temperature. After reaction for 5 h, the reaction mixture is heated to 60° C. After stirring for 24 h at 60° C, an excess of reagents is added: silver oxide (2×255 mg) and methyl iodide (2×1 ml). After heating for a further 36 hours, the reaction mixture is filtered through a sinter funnel and the filtrate is evaporated. According to the HPLC analysis, the reaction medium contains 11.5% (by internal standardization of the areas) of 7,10-dimethoxy-10-deacetylbaccatin.

Example 2

Silver oxide/methyl iodide/pyridine/toluene/10-DAB

Pyridine (8 µl, 0.1 mmol, 0.2 equiv.) and then silver oxide (255 mg, 1.1 mmol, 2.2 equiv.) are successively added to a suspension of 10-deacetylbaccatin III (272 mg, 0.5 mmol) in a toluene/methyl iodide mixture (3/2; 2.5 ml) at room temperature. The reaction mixture is then heated to 50° C. After stirring for 24 h at 60° C., an excess of reagents is added: silver oxide (255 mg, 1.1 mmol, 2.2 equiv.), pyridine (80 µl, 1 mmol, 2 equiv.) and methyl iodide (1 ml). After heating for a further 24 h, the reaction mixture is filtered through a sinter funnel and the filtrate is diluted with ethyl acetate (40 ml). This phase is washed with brine (20 ml) separated, dried over sodium sulphate and evaporated (131 mg). According to the HPLC analysis, the crude reaction product contains 12.2% (by internal standardization of the areas) of 7,10-dimethoxy-10-deacetylbaccatin.

Example 3

Silver oxide/methyl iodide/N,N-dimethylformamide/10-DAB

Silver oxide (255 mg, 1.1 mmol, 2.2 equiv.) is added to a solution of 10-deacetylbaccatin III (272 mg, 0.5 mmol) in an N,N-dimethylformamide/methyl iodide mixture (3/2; 2.5 ml) at 0° C. The mixture is allowed to return gradually to room temperature. After stirring for 24 h, the reaction mixture is diluted with diethyl ether (20 ml) and filtered through a sinter funnel. The filtrate is washed with water (20 ml). The organic phase is separated out, dried over sodium sulphate and evaporated (207 mg). According to the HPLC analysis, the crude reaction product contains 9.2% (by internal standardization of the areas) of 7,10-dimethoxy-10-deacetylbaccat in.

Example 4

Potassium hydride/methyl iodide/tetrahydrofuran/10-DAB

The potassium hydride as a 20% suspension in a mineral oil (6.0 g, 30 mmol, 3 equiv.) is prewashed with pentane.

A suspension of lo-deacetylbaccatin III (5.23 g, 10 8.5 mmol, 89% pure) in a tetrahydrofuran/methyl iodide mixture (3/2, 50 ml) is added dropwise to a suspension of potassium hydride, prewashed with pentane, in tetrahydrofuran (30 ml) at −30° C. The mixture is then allowed to return gradually to room temperature. After stirring for 3 h 30, the reaction mixture is poured into water (150 ml) and diisopropyl ether (250 ml). The mixture is filtered through a sinter funnel. The precipitate is then collected and washed separately with water (14 ml). This suspension is again filtered through a sinter funnel to give, after drying overnight in a desiccator over $P_2O_5$, 3.17 g of 7,10-dimethoxy-10-deacetylbaccatin (HPLC purity: 93% by internal standardization of the areas). The yield of isolated product is 61%.

Example 5

Potassium t-butoxide/methyl iodide/tetrahydrofuran/10-DAB

A suspension of 10-deacetylbaccatin III (544 mg, 1 mmol) in a tetrahydrofuran/methyl iodide mixture (3/2, 5 ml) is added dropwise to a suspension of potassium t-butoxide (336 mg, 3 mmol, 3 equiv.) in tetrahydrofuran (4 ml) at −30° C. The mixture is then allowed to return gradually to room temperature. After stirring for 3 h 30, HPLC analysis indicates that the reaction mixture contains 10.0% (by internal standardization of the areas) of 7,10-dimethoxy-10-deacetylbaccatin.

Example 6

Potassium hydride/methyl sulphate/tetrahydrofuran/10-DAB

The potassium hydride as a 20% suspension in a mineral oil (0.6 g, 3 mmol, 3 equiv.) is prewashed with pentane.

A suspension of 10-deacetylbaccatin III (544 mg, 1 mmol) in tetrahydrofuran (6 ml) and a solution of methyl sulphate (2.0 g, 16 mmol, 16 equiv.) in tetrahydrofuran (2 ml) are simultaneously added dropwise to a suspension of potassium hydride, prewashed with pentane, in tetrahydrofuran (3 ml) at −20° C. The mixture is then allowed to return gradually to room temperature. After reaction for 8 h, the reaction mixture is poured into water (20 ml) and placed overnight at 4° C. Diisopropyl ether (20 ml) is then added and the mixture is filtered through a sinter funnel to give 220 mg. According to the HPLC analysis, the crude reaction product contains 98% (by internal standardization of the areas) of 7,10-dimethoxy-10-deacetylbaccatin.

Example 7

Potassium hydride/trimethyloxonium tetrafluoroborate/tetrahydrofuran/10-DAB

The potassium hydride as a 20% suspension in a mineral oil (0.6 g, 3 mmol, 3 equiv.) is prewashed with pentane.

A suspension of 10-deacetylbaccatin III (544 mg, 1 mmol) in tetrahydrofuran (3 ml) is added to a suspension of potassium hydride, prewashed with pentane, and of trimethyloxonium tetrafluoroborate in tetrahydrofuran (3 mol) at −20° C. The mixture is then allowed to rise gradually to a temperature of −10° C. After reaction for two hours, a suspension of potassium hydride (2 equiv.) in tetrahydrofuran (1 ml) is added. After reaction for a further two hours, HPLC analysis indicates that the reaction mixture contains 16.3% (by internal standardization of the areas) of 7,10-dimethoxy-10-deacetylbaccatin.

Example 8

Potassium hydride/methyl iodide/1,2-dimethoxyethane/10-DAB

The potassium hydride as a 20% suspension in a mineral oil (0.6 g, 3 mmol, 3 equiv.) is prewashed with pentane.

A solution of 10-deacetylbaccatin III (544 mg, 1 mmol) in a 1,2-dimethoxyethane/methyl iodide mixture (3/1, 8 ml) is added dropwise to a suspension of potassium hydride, prewashed with pentane, in 1,2-dimethoxyethane (3 ml) at −20° C. The mixture is then allowed to return gradually to room temperature. After stirring for 6 h 30, HPLC analysis indicates that the reaction mixture contains 28.1% (by internal standardization of the areas) of 7,10-dimethoxy-10-deacetylbaccatin.

Example 9

Potassium hydride/methyl iodide/tetrahydrofuran/compound (V) with A=(id) ($R_1$=phenyl, $R_2$=H, $R_3$=t-butoxycarbonyl, $R_4$=4-methoxyphenyl)

The potassium hydride as a 20% suspension in a mineral oil (0.145 g, 2.4 equiv.) is prewashed with pentane.

A suspension of 4-acetoxy-2α-benzoyloxy-5β,20-epoxy-1,7β,10β-trihydroxy-9-oxotax-11-en-13α-yl (2R,4S,5R)-3-tert-butoxycarbonyl-2-(4-methoxyphenyl)-4-phenyl-5-oxazolidinecarboxylate (284 mg, 0.3 mmol) in a tetrahydrofuran/methyl iodide mixture (5/3, 1.6 ml) is added dropwise to a suspension of potassium hydride, prewashed with pentane, in tetrahydrofuran (0.7 ml) at −78° C. The mixture is then allowed to rise gradually to a temperature of −15° C. After stirring for 3 h 30, the reaction mixture is poured into water (15 ml) and ethyl acetate (15 ml). The organic phase is separated out, washed with brine (15 ml), dried over sodium sulphate, filtered and evaporated (232 mg). HPLC analysis of the crude product gives an assayed yield of 39% of 4-acetoxy-2α-benzoyloxy-5β, 20-epoxy-1- hydroxy-9-oxo-7β,10β-dimethoxytax-11-en-13α-yl (2R,4S, 5R)-3-tert-butoxycarbonyl-2-(4-methoxyphenyl)-4-phenyl-5-oxazolidinecarboxylate.

Example 10

Sodium hydride/methyl iodide/tetrahydro-furan/10-DAB

The sodium hydride as a 55% suspension in a mineral oil (0.13 g, 3 mmol, 3 equiv.) is prewashed with pentane.

A suspension of 10-deacetylbaccatin III (544 mg, 1 mmol) in a tetrahydrofuran/methyl iodide mixture (3/2, 5 ml) is added dropwise to a suspension of sodium hydride, prewashed with pentane, in tetrahydrofuran (3 ml) at 0° C. The mixture is then allowed to return gradually to room temperature. After stirring for 7 h 30, the reaction mixture is poured into water (25 ml) and diisopropyl ether (25 ml). A precipitate appears, which is filtered off on a sinter funnel. 57 mg of product are thus recovered containing 67% (by internal standardization of the areas) of 7,10-dimethoxy-10-deacetylbaccatin.

Example 11 n-butyllithium/potassium t-butoxide/tetra-hydrofuran/10-DAB

A solution of n-butyllithium in hexane (2 ml, 3 mmol, 3 equiv.) is evaporated under vacuum. The residue is taken up in tetrahydrofuran (3 ml), precooled to −78° C. Potassium t-butoxide (336 mg, 3 mmol, 3 equiv.) is then added, followed by addition of a suspension of 10-deactyl baccatin III (544 mg, 1 mmol) in a tetrahydrofuran/methyl iodide mixture (5 ml, 3/2). The mixture is then allowed to return gradually to room temperature. After reaction for 3 h 45, the mixture is poured into water (10 ml) and diisopropyl ether (10 ml). After crystallization overnight at 4° C., 75 mg of crystals are recovered containing 61% (by internal standardization of the areas) of 7,10-dimethoxy-10-deacetylbaccatin.

Example 12 n-butyllithium/potassium t-butoxide/diisopropylamine/tetrahydrofuran/10-DAB

A solution of n-butyllithium in hexane (2 ml, 3 mmol, 3 equiv.) is evaporated under vacuum. The residue is taken up with a solution of diisopropylamine (0.5 ml, 3 mmol, 3 equiv.) in tetrahydrofuran (3 ml), precooled to −78° C. Potassium t-butoxide (336 mg, 3 mmol, 3 equiv.) is then added, followed by addition of a suspension of 10-deacetylbaccatin III (544 mg, 1 mmol) in a tetrahydrofuran/methyl iodide mixture (5 ml, 3/2). The mixture is then allowed to return gradually to room temperature. After reaction for 19 h, HPLC analysis indicates that the reaction mixture contains 24% (by internal standardization of the areas) of 7,10-dimethoxy-10-deacetylbaccatin.

Example 13

Sodium amide/t-butanol/tetrahydrofuran/10-DAB

A suspension of sodium amide (173 mg, 4 mmol, 4 equiv.) and of t-butanol (0.13 ml, 1.3 mmol, 1.3 equiv.) in tetrahydrofuran (2 ml) is heated at 45° C. for 2 h. After cooling to room temperature, the mixture is cooled to −50° C. and a suspension of 10-deacetylbaccatin III (544 mg, 1 mmol) in a tetrahydrofuran/methyl iodide mixture (3/2, 5 ml) is added dropwise. The mixture is allowed to rise gradually to −20° C. After stirring for 2 h 20, the mixture is poured into water (10 ml) and diisopropyl ether (10 ml). The precipitate is filtered off on a sinter funnel to give 160 mg of crude product containing 37% (by internal standardization of the areas) of 7,10-dimethoxy-10-deacetylbaccatin.

Example 14

Trimethyloxonium tetrafluoroborate/1,8-bis(dimethylamino)naphthalene/4 Å sieves/10-DAB 1,8-bis(dimethylamino)naphthalene (514 mg, 2.4 mmol, 12 equiv.), 4 Å molecular sieves (700 mg) and trimethyloxonium tetrafluoroborate (296 mg, 2 mmol, 10 equiv.) are successively added to a suspension of 10-deacetylbaccatin III (109 mg, 0.2 mmol) in dichloromethane (4 ml) at 25° C. After stirring for 24 h at room temperature, HPLC analysis indicates that the reaction mixture contains 7,10-dimethoxy-10-deacetylbaccatin in an assayed yield of 17%.

Example 15

1,8-bis(dimethylamino)naphthalene (1.2744 g, 5.95 mmol, 12.8 equiv.) and trimethyloxonium tetrafluoroborate (0.7598 g, 14 mmol, 11 equiv.) are successively added to a suspension of 10-deacetylbaccatin III (0.2876 g, 0.46 mmol) in ethyl acetate (7.8 ml) at 20° C. After stirring for 2 hours 20 minutes at a temperature of between 45–50° C., HPLC analysis indicates that the reaction mixture contains 7,10-dimethoxy-10-deacetylbaccatin in an assayed yield of 62%. Analyses for the compound 7,10-dimethoxy-10-deacetylbaccatin III The NMR analyses were carried out on a Bruker AM 360 spectrometer operating at 360 MHz for proton and 90 MHz for carbon-13, and equipped with a 5 mm proton/carbon-13 dual probe. The chemical shifts are expressed in ppm; DMSO is used as external reference (2.44 ppm in the proton spectrum and 39.5 ppm in the carbon spectrum). The temperature is controlled by a variable-10 temperature unit to 300 K.

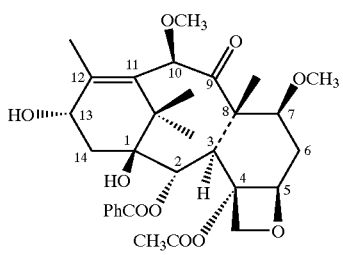

| Position | ¹H NMR δ (ppm) | multiplicity | J (Hz) | ¹³C NMR δ (ppm) |
|---|---|---|---|---|
| 1 | — | — | — | 75.2 |
| 2 | 5.34 | doublet | 7.2 | 74.3 |
| 3 | 3.71 | doublet | 7.2 | 47.0 |
| 4 | — | — | — | 80.0 |
| 5 | 4.93 | doublet | 9.1 | 83.2 |
| 6 | 1.44/2.64 | multiplet | — | 31.7 |
| 7 | 3.76 | doubled doublet | 10.5/ 6.5 | 80.4 |
| 8 | — | — | — | 56.6 |
| 9 | — | — | — | 205.3 |

-continued

| Position | ¹H NMR δ (ppm) | multiplicity | J (Hz) | ¹³C NMR d (ppm) |
|---|---|---|---|---|
| 10 | 4.70 | singlet | — | 82.7 |
| 11 | — | — | — | 132.7 |
| 12 | — | — | — | 143.9 |
| 13 | 4.61 | multiplet | — | 66.1 |
| 14 | 2.13 | multiplet | — | 39.3 |
| 15(CH₃) | 0.90 | singlet | — | 20.5 |
|  |  |  |  | 26.9 |
| 1(OH) | 4.33 | singlet | — | — |
| 2(PhCOO) | 7.5(2H) | triplet | — | 165.1(C=O) |
|  | 7.6(1H) | triplet | — | 130.1/129.4 |
|  | 8.0(ortho C=O) | doublet | 7.5 | 128.6/133.1 |
| 4(Ac) | 2.15 | singlet | — | 169.6 |
|  |  |  |  | (C=O)22.3 |
| 4(CH₂O) | 3.99 | AB system | not determined | 76.8 |
| 7(OCH₃) | 3.17 | singlet | — | 56.4 |
| 8(CH₃) | 1.47 | singlet | — | 10.0 |
| 10(OCH₃) | 3.25 | singlet | — | 56.0 |
| 12(CH₃) | 1.93 | singlet | — | 15.0 |
| 13(OH) | 5.25 | doublet | 4.5 | — |

Ms: Direct introduction; ionization mode ESI+

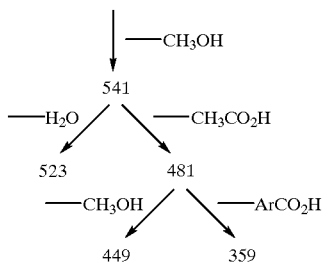

IR (KBr):

| | |
|---|---|
| 3552.5 cm⁻¹ | Alcoholic O—H (secondary) |
| 3434.9 cm⁻¹ | Alcoholic O—H (tertiary) |
| 2972.2–2931.5–2892.6 cm⁻¹ | Hydrocarbon skeleton |
| 2826.9 cm⁻¹ | C—H of the O—CH₃ units |
| 1716–1705.3 cm⁻¹ | C=O of the OAc and ketone units |
| 1269.7–1250.8 cm⁻¹ | Aromatic ether C—O |
| 1098.3–1068.7 cm⁻¹ | C—O of the alcohols and cyclic ether |

We claim:

1. A process, comprising the step of alkylating the hydroxyl functions at the 7-position and 10-position of a compound of formula (V):

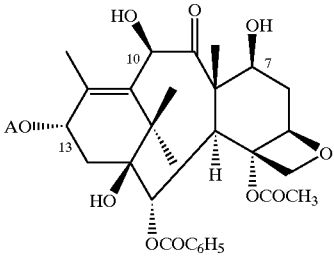

wherein A represents hydrogen, a side chain of formula (Ic), or an oxazolidine of formula (Id):

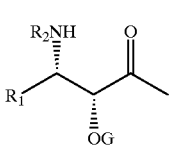

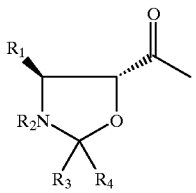

wherein:
G represents a hydroxyl protecting group;
R₁ represents:
a straight or branched alkyl radical containing 1 to 8 carbon atoms, a straight or branched alkenyl radical containing 2 to 8 carbon atoms, a straight or branched alkynyl radical containing 2 to 8 carbon atoms, a cycloalkyl radical containing 3 to 6 carbon atoms, a phenyl or α- or β-naphthyl radical, unsubstituted or substituted with one or more atoms or radicals chosen from halogen atoms and alkyl, alkenyl, alkyny, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro and trifluoromethyl radicals, or
a 5-membered aromatic heterocycle containing one or more hetero atoms, which may be identical or different, chosen from nitrogen, oxygen or sulphur atoms, said 5-membered aromatic heterocycle being unsubstituted or substituted with one or more of halogen atoms or alkyl, aryl, amino, alkylamino, dialkylamino, alkoxycarbonylamino, acyl, arylcarbonyl, cyano, carboxyl, carbamoyl, alkylcarbamoyl, dialkylcarbamoyl, or alkoxycarbonyl radicals,
wherein when R₁ is a substituted phenyl radical, a substituted α- or β-naphthyl radical, or a substituted aromatic heterocycle, the alkyl radical substituent or the alkyl portion of another radical substituent contains 1 to 4 carbon atoms, the alkenyl or alkynyl radical substituent contains 2 to 8 carbon atoms, and the aryl radical substituent is a phenyl or α- or β-naphthyl radical;

$R_2$ represents:
1) a benzoyl radical, unsubstituted or substituted with one or more atoms or radicals, which may be identical or different, chosen from halogen atoms and alkyl radicals containing 1 to 4 carbon atoms, alkoxy radicals containing 1 to 4 carbon atoms or trifluoromethyl, thenoyl or furoyl radicals, or
2) a radical $R'_2$—C—CO—, wherein $R'_2$ represents:
   an alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, these radicals being unsubstituted or substituted with one or more substituents chosen from halogen atoms and hydroxyl radicals, alkoxy radicals containing 1 to 4 carbon atoms, dialkylamino radicals in which each alkyl part contains 1 to 4 carbon atoms, piperidino or morpholino radicals, 1-piperazinyl radicals (unsubstituted or substituted in position 4 with an alkyl radical containing 1 to 4 carbon atoms or with a phenyl alkyl radical in which the alkyl part contains 1 to 4 carbon atoms), cycloalkyl radicals containing 3 to 6 carbon atoms, cycloalkenyl radicals containing 4 to 6 carbon atoms, phenyl radicals (unsubstituted or substituted with one or more atoms or radicals chosen from halogen atoms and alkyl radicals containing 1 to 4 carbon atoms or alkoxy radicals containing 1 to 4 carbon atoms), cyano or carboxyl radicals or alkoxycarbonyl radicals in which the alkyl part contains 1 to 4 carbon atoms,
   a phenyl or α- or β-naphthyl radical, unsubstituted or substituted with one or more atoms or radicals chosen from halogen atoms and alkyl radicals containing 1 to 4 carbon atoms or alkoxy radicals containing 1 to 4 carbon atoms or a 5-membered aromatic heterocyclic radical preferably chosen from furyl and thienyl radicals,
   or a saturated heterocyclic radical containing 4 to 6 carbon atoms, unsubstituted or substituted with one or more alkyl radicals containing 1 to 4 carbon atoms; and $R_3$ and $R_4$, which may be identical or different, represent: hydrogen or alkyl, aryl, halo, alkoxy, arylalkyl, alkoxyaryl, haloalkyl or haloaryl radicals, or $R_3$ and $R_4$ together form a 4- to 7-membered ring;

wherein the alkylation is carried out in the presence of:
(i) an alkylating agent, wherein the alkylating agent is an alkyl halide, an alkyl sulphate, or an oxonium; and
(ii) an anionization agent.

2. A process according to claim 1, wherein the compound of formula (V) is 10-deacetylbaccatin.

3. A process according to claim 1, wherein the alkylating agent is a boric salt of a trialkyloxonium.

4. A process according to claim 1, wherein the alkylating agent is trimethyloxonium tetrafluoroborate.

5. A process according to claim 1, wherein the alkylating agent is an alkyl iodide.

6. A process according to claim 1, wherein the alkylating agent is methyl iodide.

7. A process according to claim 1, wherein the alkylating agent is methyl sulphate.

8. A process according to claim 1, wherein the anionization agent is a strong base in anhydrous medium.

9. A process according to claim 8, wherein the strong base is an alkali metal hydride, an alkali metal alkoxide, silver oxide, 1,8-bis(dimethylamino)naphthalene, an alkali metal amide mixed with an alkali metal t-butoxide, or an alkyl-lithium mixed with an alkali metal t-butoxide.

10. A process according to claim 8, wherein the strong base is sodium or potassium hydride.

11. A process according to claim 8, wherein the strong base is potassium hydride.

12. A process according to claim 8, wherein the strong base is potassium tert-butoxide.

13. A process according to claim 1, wherein the alkylating agent is methyl iodide and the anionization agent is potassium hydride.

14. A process according to claim 1, wherein the reaction is carried out in an organic medium under reaction conditions wherein the organic medium is inert.

15. A process according to claim 14, wherein the organic medium is an ether.

16. A process according to claim 14, wherein the organic medium is tetrahydrofuran or dimethoxyethane.

17. A process according to claim 1, wherein the alkylation is carried out in the presence of silver oxide and an aromatic or polar aprotic solvent.

18. A process according to claim 1, wherein the alkylation is carried out in the presence of a mixture of 1,8-bis(dimethylamino)-naphthalene, trimethyloxonium tetrafluoroborate, and ethyl acetate.

19. A process according to claim 1, wherein the anionization agent and the substrate are present in a molar ratio of at least about 2.

20. A process according to claim 1, wherein the anionization agent and the substrate are present in a molar ratio of from about 2 to about 20.

21. A process according to claim 1, wherein the alkylating agent and the substrate are present in a molar ratio of at least about 2.

22. A process according to claim 1, wherein the alkylating agent and the substrate are present in a molar ratio of from about 2 to about 40.

23. A process according to claim 1, wherein the alkylation is carried out at a reaction temperature of from −30° C. to 80° C.

24. A process according to claim 1, wherein the alkylation step involves simultaneous alkylation of the hydroxyl functions at the 7-position and 10-position of the compound of formula (V).

* * * * *